(12) United States Patent
Pratley et al.

(10) Patent No.: US 6,290,932 B2
(45) Date of Patent: *Sep. 18, 2001

(54) AQUEOUS HAIR AEROSOL STYLING AIDS

(75) Inventors: Stuart Keith Pratley; Keith Leslie Rutherford, both of Wirral (GB)

(73) Assignee: Unilever Home & Personal Care USA, division of Conopco, Inc., Chicago, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/456,193

(22) Filed: Dec. 7, 1999

(30) Foreign Application Priority Data

Dec. 10, 1998 (GB) .................................................. 9827222

(51) Int. Cl.$^7$ ...................................................... A61K 9/12
(52) U.S. Cl. .......................... 424/45; 424/47; 424/70.1; 424/70.12; 424/70.21; 424/70.22; 424/70.27; 424/70.31; 424/70.11; 424/DIG. 1; 424/DIG. 2; 514/63
(58) Field of Search .................... 424/43, 45, 47, 424/70.1, 70.12, 70.21, 70.22, 70.27, 70.31, 70.11, DIG. 1, DIG. 2; 514/63

(56) References Cited

U.S. PATENT DOCUMENTS 5,567,428 * 10/1996 Hughes .
5,578,298   11/1996 Bertheaume et al. .
5,750,122    5/1998 Evans et al. .
6,001,339 * 12/1999 Finel et al. .

FOREIGN PATENT DOCUMENTS 0796611   9/1997 (EP) .
0818190   1/1998 (EP) .
98/18433   5/1998 (WO) .
98/50007  11/1998 (WO) .

OTHER PUBLICATIONS

M. S. Starch (1984). *Drug & Cosmetic Industry*, vol. 134, No. 6, pp. 38–44 and 102.*

M. A. Johnsen (1992). *Spray Techology & Marketing*, Jun. issue, pp. 32–39.*

* cited by examiner

Primary Examiner—Raj Bawa
(74) Attorney, Agent, or Firm—Matthew Boxer

(57) ABSTRACT

The invention provides an aqueous hair styling aid comprising a volatile silicone selected from cyclic silicones having the general formula (I):

$$[(CH_3)_2Si-O-]_n \qquad (I)$$

wherein n=3–7, and short chain linear silicones having the general formula (II):

$$(CH_3)_3Si-O-[Si(CH_3)_2O]_nSi(CH_3)_3 \qquad (II)$$

wherein n=1–7;

together with hairstyling polymer, surfactant and at least 5% water.

6 Claims, No Drawings

AQUEOUS HAIR AEROSOL STYLING AIDS

BACKGROUND OF THE INVENTION

1. Field of the Invention

This invention relates to aqueous hair styling aids, especially hair styling mousses, which incorporate a volatile silicone and which have improved strength and durability of hair hold and superior sensory feel.

2. Background and Prior Art

Hair styling aids such as hair styling mousses provide human hair with a temporary set which can be removed by water or by shampooing, and function by applying a thin film of a resin or gum onto the hair to adhere adjacent hairs together so that they retain the particular shape or configuration at the time of application.

Conventional hair styling mousses typically utilise a hair setting polymer, water, surfactant and propellant gas, with optional adjuvants such as aesthetic agents, fragrance and hair conditioning agents. The conditioning agents used have included silicone-type materials.

EP 0 523 388 discloses an aqueous hair styling aid or mousse composition incorporating a non-volatile silicone compound or other water-insoluble, emulsifiable conditioning agent. The preferred non-volatile silicone compound is a 3:1 mixture of a low molecular weight polydimethylsiloxane fluid and a higher molecular weight polydimethylsiloxane gum.

EP 0 205 306 discloses the use of high molecular weight silicone materials in styling mousses. These are defined as polydiorganosiloxanes having a viscosity of at least 100,000 cst. The high molecular weight silicone is dissolved in the propellant phase prior to filling the aerosol container.

A problem is that those silicone materials which are typically used as conditioning agents in hair care applications tend to make the hair too soft to form and retain a style.

CA 1 214 106 describes that the use of cyclic silicone fluids in ethanol-based aerosol hairspray compositions provides increased holding power and softer feel compared with formulations containing silicone glycols as plasticising materials for the hairspray resin. However this publication is concerned entirely with ethanol-based systems, and none of the formulations disclosed contain any water. Increasingly with the advent of legislation concerning the volatile organic content of hairsprays, it has become desirable to formulate systems with relatively high water content.

EP 0 657 157 A1 discloses that particular volatile linear and cyclic alkylmethylsilicones can be substituted for a portion of the water in a low VOC compliant styling aid formulation, and form compatible systems when combined with water and ethanol in certain prescribed ranges of these three ingredients. This publication is concerned specifically with alkylmethylsilicones having in the molecule methyl and alkyl groups which include six, seven or eight carbon atoms.

The present inventors have surprisingly discovered that the strength and durability of hair hold delivered by a hair styling resin in an aqueous hair styling mousse can be significantly increased by the inclusion in the formulation of certain volatile silicones selected from linear and cyclic dimethylsilicones. Advantageously, hair styling mousses of the invention also exhibit superior sensory feel.

SUMMARY OF THE INVENTION

The present invention provides an aqueous hair styling aid comprising:

(i) from 0.1% to 10% by weight, based on total weight, of a volatile silicone selected from cyclic silicones having the general formula (I):

wherein n=3–7, and short chain linear silicones having the general formula (II):

wherein n=1–7;

(ii) from 0.1% to 10% by weight, based on total weight, of a hair styling polymer;

(iii) from 0.01% to 5% by weight, based on total weight, of a surfactant;

(iv) at least 5% by weight, based on total weight, of water; and (v) from 0% to 30% by weight, based on total weight, of an aerosol propellant, in which the weight ratio of (i):(ii) ranges from 5:1 to 1:10.

DETAILED DESCRIPTION

Volatile Silicone

The term "volatile" as used herein means that the material in question has a measurable vapour pressure.

The viscosity of the volatile silicone is generally less than 10 cst at 25° C. Viscosity can be measured by means of a glass capillary viscometer as set out further in Dow Corning Corporate Test Method CTM004 Jul. 20, 1970.

Preferred cyclic silicones are dimethyl siloxane cyclic tetramer (n=4 in general formula (I)) and dimethyl siloxane cyclic pentamer (n=5 in general formula (I)).

Preferred short chain linear silicones generally have viscosities of less than 5 cst at 25° C.

Silicones of the above described types are widely available, e.g. from Dow Corning as DC 244, 245, 344, 345 and 200 fluids; Union Carbide as Silicone 7202 and 7158, and Stauffer Chemical as SWS-03314.

The amount of the volatile silicone may range from 0.1 to 10%, preferably 0.5 to 5% by weight of the total composition.

Hair Styling Polymer

The hair styling polymers employed in compositions of the present invention should be capable of forming a film and holding the hair of the user in place after evaporation of the volatile components of the hair styling composition.

Hair styling polymers are well known articles of commerce and many such polymers are available commercially which contain moieties which render the polymers cationic, anionic, amphoteric or nonionic in nature.

The amount of the polymer may range from 0.5 to 10%, preferably 0.75 to 6% by weight of the total composition.

Examples of anionic hair styling polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:

RESYN® 28-2930 available from National Starch (vinyl acetate/crotonic acid/vinyl neodecanoate copolymer);

Ultrahold® 8 available from BASF (CTFA designation Acrylates/acrylamide copolymer);

the Gantrez® ES series available from ISP corporation (esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP 0 619 111 A1 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation— specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are crosslinked silicone resins or gums. Specific examples include rigid silicone polymers such as those described in EP-A-240 350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:

copolymers of N-vinylpyrrolidone and dimethylaminoethyl methacrylate, available from ISP Corporation as Copolymer 845, Copolymer 937 and Copolymer 958;

copolymers of vinylpyrrolidone and dimethylaminopropylacrylamide or methacrylamide, available from ISP Corporation as Styleze CC10;

Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;

Polyquaternium-16 (formed from methylvinylimidazolium chloride and vinylpyrrolidone), available from BASF as Luviquat® FC 370, FC 550, FC 905 and HM-552;

Polyquaternium-46 (prepared by the reaction of vinylcaprolactam and vinylpyrrolidone with methylvinylimidazolium methosulphate), available from BASF as Luviquat®Hold.

The preferred hair styling polymers in compositions of the invention are selected from the group consisting of Polyquaternium-11, Polyquaternium-16, Polyquaternium-46 and mixtures thereof.

With certain of the above-described polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as lauramidopropyl dimethylamine may be employed, as is described in U.S. Pat. No. 4,874,604. Mixtures of any of the above neutralising agents may be used. Amounts of the neutralising agents will range from about 0.001 to about 10% by weight of the total composition.

Weight Ratio

In compositions of the invention, the weight ratio of volatile silicone to hair styling polymer ranges from 5:1 to 1:10. Preferably, the weight ratio ranges from 2:1 to 1:4, optimally from 1:1 to 1:2.

Surfactant

In addition to the volatile silicone and the hair styling polymer, the aqueous hair styling aid of the invention also includes a surfactant in an amount ranging from 0.01% to 5%, preferably from 0.01% to 1%, most preferably from 0.02% to 0.8% by weight based on total weight.

Surfactants are generally classified as nonionic, anionic, cationic, amphoteric or zwitterionic according to their ionic behaviour in aqueous solution.

Examples of nonionic surfactants are condensation products of aliphatic ($C_8$–$C_{18}$) primary or secondary linear or branched chain alcohols or phenols with alkylene oxides, usually ethylene oxide and generally having from 6 to 50 ethylene oxide groups. Specific examples are steareth-40, steareth-50, ceteareth-30, ceteareth-40, ceteareth-50 and mixtures thereof. Suitable commercially available examples of these materials include Unicol SA-40 (Universal Preserv-A-Chem), Empilan KM50 (Albright and Wilson), NONION PS-250 (Nippon Oils & Fats), Volpo CS50 (Croda Inc), and Incropol CS-50 (Croda Inc).

Other suitable nonionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates. Specific examples are polyoxyethylene (9) nonyl phenyl ether, Polysorbate 20, Polysorbate 80 and mixtures thereof.

Examples of anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of cationic surfactants are cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, (and the corresponding hydroxides thereof), and those materials having the CTFA designations Quaternium-5, Quaternium-31 and Quaternium-18.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Preferred amphoteric surfactants are lauryl amine oxide, cocodimethyl sulphopropyl betaine, lauryl betaine, sodium cocamphopropionate, and especially cocamidopropyl betaine.

The surfactants in compositions of the invention are most preferably selected from one or more nonionic surfactants. Surfactants selected from anionic, cationic, amphoteric and zwitterionic surfactants may suitably be used in conjunction with these nonionic surfactants, to improve, for example, foaming power and/or foam stability.

Water

Compositions of the present invention will also include water (preferably distilled or deionised), as a solvent or carrier for the polymers and other components. Water will typically be present in amounts ranging from 30% to 98%, preferably from 60% to 95%, most preferably from 80% to 95% by weight based on total weight.

Alcohol may optionally be employed as a co-solvent in compositions of the invention as this can enhance the performance of the styling composition. A suitable alcohol is an aliphatic straight or branched chain monohydric alcohol having 2 to about 4 carbon atoms. Isopropanol and especially ethanol are preferred. A suitable level for the alcohol is up to 20%, preferably from 5% to 15%, by weight based on total weight.

Product Form

Compositions of the invention may suitably be in aerosol form. A particularly preferred product form is an aerosol hair mousse. Aerosol hair mousse compositions are emitted from the aerosol container as a foam which is then typically worked through the hair with fingers or a hair styling tool and either left on the hair or rinsed out.

Aerosol-form compositions of the invention will include an aerosol propellant which serves to expel the other materials from the container, and forms the mousse character in mousse compositions. The aerosol propellant included in styling compositions of the present invention can be any liquefiable gas conventionally used for aerosol containers. Examples of suitable propellants include dimethyl ether and hydrocarbon propellants such as propane, n-butane and isobutane. The propellants may be used singly or admixed. Water insoluble propellants, especially hydrocarbons, are preferred because they form emulsion droplets on agitation and create suitable mousse foam densities.

The amount of the propellant used is governed by normal factors well known in the aerosol art. For mousses the level of propellant is generally up to 30%, preferably from 2% to 30%, most preferably from 3% to 15% by weight based on total weight of the composition. If a propellant such as dimethyl ether includes a vapour pressure suppressant (e.g. trichloroethane or dichloromethane), for weight percentage calculations, the amount of suppressant is included as part of the propellant.

The method of preparing aerosol hair styling mousse compositions according to the invention follows conventional aerosol filling procedures. The composition ingredients (not including the propellant) are charged into a suitable pressurisable container which is sealed and then charged with the propellant according to conventional techniques.

Compositions of the invention may also take a non-foaming product form, such as a hair styling cream or gel. Such a cream or gel will include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid crosslinked with polyallylsucrose as described in U.S. Pat. No. 2,798,053. These polymers are provided by B.F. Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone,hydroxypropyl guar gum, starch and starch derivatives, and other thickeners, viscosity modifiers, gelling agents, etc. It is also possible to use inorganic thickeners such as bentonite or laponite clays.

The aqueous hair styling aids of the invention can contain a variety of nonessential, optional components suitable for rendering the compositions more aesthetically acceptable or to aid use, including discharge from the container, of the product. Such conventional optional ingredients are well known to those skilled in the art, e.g. preservatives such as benzyl alcohol, methyl paraben, propyl paraben and imidazolidinyl urea, fatty alcohols such as cetearyl alcohol, cetyl alcohol and stearyl alcohol, pH adjusting agents such as citric acid, succinic acid, sodium hydroxide and triethanolamine, colouring agents such as any of the FD&C or D&C dyes, perfume oils, chelating agents such as ethylenediamine tetraacetic acid, and polymer plasticising agents such as glycerin and propylene glycol.

The invention also provides a method of styling hair by applying thereto an aqueous hair styling aid as is hereinabove described.

The following Examples further illustrate the preferred embodiments of the invention. All percentages referred to are by weight unless otherwise indicated.

EXAMPLES

Example 1 and Comparative Example A

Hair styling mousses were prepared having ingredients as shown in the following Table:

| Ingredient (wt %) | Example 1 | Comparative Example A |
|---|---|---|
| Luviquat ® FC550[1] | 7.5 | 7.5 |
| Ethanol | 8.0 | 8.0 |
| Water | to 100 | to 100 |
| CAP40[2] | 8.0 | 8.0 |
| Tween ® 80[3] | 0.4 | 0.4 |
| Dow Corning ® 245 Fluid[4] | 3.0 | None |

[1]Polyquaternium-16 (aqueous solution, 40% a.i.), ex BASF.
[2]Propane/butane
[3]Polysorbate 80, ex ICI Surfactants
[4]Cyclomethicone, ex Dow Corning In a panellist evaluation for sensory properties, Example 1 according to the invention outperformed Comparative Example A on wet styling, wet hair feel and dry hair feel.

Examples 2 and 3

The following Examples illustrate further hair styling mousses according to the invention.

| Ingredient (wt %) | Example 2 | Example 3 |
|---|---|---|
| Luviquat ® FC550[1] | 9.3 | 4.65 |
| Ethanol | None | 7.43 |
| Water | to 100 | to 100 |
| CAP40[2] | 7.0 | 7.0 |
| Tween ® 80[3] | 0.3 | 0.3 |
| Dow Corning ® 245 Fluid[4] | 2.79 | 0.93 |
| Cross-linked silicone[5] | None | 6.78 |

[5]An emulsion polymerised dimethiconol containing 0.6% cross-linking, 55% aqueous emulsion, ex Dow Corning.

What is claimed is:

1. An aerosal aqueous hair styling aid consisting of essentially of:
   (i) from 0.1% to 10% by weight, based on total weight, of a volatile silicone selected from the cyclic silicones having the general formula (I):

$$[(CH_3)_2Si-O-]_n \quad (I)$$

wherein n=3–7, and short chain linear silicones having the general formula (II):

$$(CH_3)_3SI-O-[Si(CH_3)_2O]_nSi(CH_3)_3 \quad (II)$$

wherein n=1–7;
   (ii) from 0.1% to 10% by weight, based on total weight, of a hair styling polymer selected from the group consisting of cross-linked silicone gums, Polyquaternium-11, Polyquaternium-16, Polyquaternium-46, and mixture thereof;
   (iii) from 0.01% to 1% by weight, based on total weight, of a nonionic surfactant;
   (iv) at least 5% by weight, based on total weight, of water; and
   (v) from 2% to 30% by weight, based on total weight, of an aerosol propellant selected from the group consisting of dimethyl ether, propane, n-butane, isobutane and mixtures thereof;
   in which the weight ratio of (i):(ii) ranges from 2:1 to 1:4.

2. An aqueous hair styling aid according to claim 1, in which the volatile silicone is a cyclic silicone selected from dimethyl siloxane cyclic tetramer or dimethyl siloxane cyclic pentamer.

3. An aqueous hair styling aid according to claim 1, in which the amount of water ranges from 30% to 98% by weight based on total weight.

4. An aqueous hair styling aid according to claim 1, wherein the weight ratio of volatile silicone to hair styling polymer ranges from 1:1 to 1:2.

5. An aqueous hair styling aid according to claim 3, wherein the amount of water ranges from 60% to 95% by weight based on total weight.

6. An aqueous hair styling aid according to claim 5, wherein the amount of water ranges 80% to 95% by weight based on total weight.

* * * * *